United States Patent
Sakamoto et al.

(10) Patent No.: US 7,667,059 B2
(45) Date of Patent: Feb. 23, 2010

(54) PROCESS FOR PRODUCING GLYCERIN AND FATTY ALCOHOL VIA HYDROGENATION

(75) Inventors: Toru Sakamoto, Wakayama (JP);
Nobuhiro Tatsumi, Wakayama (JP);
Hideaki Ueoka, Ibaraki (JP)

(73) Assignee: Kao Corporation, Tokyo (JP)

( * ) Notice: Subject to any disclaimer, the term of this patent is extended or adjusted under 35 U.S.C. 154(b) by 273 days.

(21) Appl. No.: 11/367,340

(22) Filed: Mar. 6, 2006

(65) Prior Publication Data
US 2006/0205965 A1  Sep. 14, 2006

(30) Foreign Application Priority Data
Mar. 8, 2005 (JP) ............... 2005-063359

(51) Int. Cl.
*C11C 3/10* (2006.01)
(52) U.S. Cl. .......... 554/169; 568/864
(58) Field of Classification Search ............ None
See application file for complete search history.

(56) References Cited

U.S. PATENT DOCUMENTS

| 2,094,127 | A |   | 9/1937  | Lazier |
| 2,109,844 | A |   | 3/1938  | Lazier |
| 2,241,417 | A |   | 5/1941  | Normann et al. |
| 4,307,026 | A | * | 12/1981 | Kuiper ............... 554/145 |
| 4,942,266 | A | * | 7/1990  | Fleckenstein et al. ....... 568/864 |
| 5,364,986 | A |   | 11/1994 | Demmering et al. |
| 5,475,160 | A |   | 12/1995 | Singleton et al. |

FOREIGN PATENT DOCUMENTS

DE  1 668 219  3/1972

OTHER PUBLICATIONS

U.S. Appl. No. 11/817,921, filed Sep. 6, 2007, Sakamoto, et al.

* cited by examiner

*Primary Examiner*—Deborah D Carr
(74) *Attorney, Agent, or Firm*—Oblon, Spivak, McClelland, Maier & Neustadt, L.L.P.

(57) ABSTRACT

The invention relates to a process for producing a fatty alcohol and glycerin by hydrogenation reaction of fats and oils in the presence of a catalyst, wherein the reaction is carried out in the coexistence of an organic solvent.

14 Claims, 1 Drawing Sheet

_US 7,667,059 B2_

PROCESS FOR PRODUCING GLYCERIN AND FATTY ALCOHOL VIA HYDROGENATION

TECHNICAL FIELD

The present invention relates to a process for producing an alcohol by hydrogenation reaction of fats and oils.

BACKGROUND OF THE INVENTION

Conventionally, a process for producing fatty alcohols by catalytically hydrogenating lower alcohol fatty esters obtained by transesterification of fats and oils with a lower monoalcohol, preferably methanol, is used for industrial production of fatty alcohols. Alternatively, a method of catalytically hydrogenating wax esters obtained by esterifying hydrolyzed fatty acids and fatty alcohols is also used. These two-stage processes are economically excellent because valuable glycerin can be obtained with high yield and high purity.

On one hand, the direct catalytic hydrogenation of fats and oils enables an industrially important product fatty alcohol to be directly obtained from naturally occurring fats and oils, but is not so used in industrial production. This is because a side reaction wherein initially formed glycerin is hydrogenated on the surface of a catalyst occurs in the direct catalytic hydrogenation of fats and oils, and thus glycerin cannot be obtained in high yield, so the direct catalytic hydrogenation process cannot compete economically with the 2-stage process. This is one reason that the process of directly hydrogenating fats and oils is not used in industrial scale.

Methods of obtaining a fatty alcohol by directly hydrogenating fats and oils are described in for example U.S. Pat. No. 2,094,127, U.S. Pat. No. 2,109,844 and U.S. Pat. No. 2,241,417. DE-A 1668219 describes a method of hydrogenating fats and oils obtained from fats and oils. U.S. Pat. No. 5,364,986 and U.S. Pat. No. 5,475,160 also describe methods of directly hydrogenating fats and oils, and in these methods, the direct hydrogenation of fats and oils into fatty alcohols is conducted by using a copper-based catalyst under relatively mild reaction conditions.

SUMMARY OF THE INVENTION

The present invention relates to a process for producing a fatty alcohol and glycerin, including the step of hydrogenating fats and oils in the presence of a catalyst and in the coexistence of an organic solvent.

In other words, the invention provides a process for producing an aliphatic alcohol and/or glycerin, including a step of hydrogenating (hydrogenation reacting) fats and/or oils in the presence of a catalyst and an organic solvent.

DETAILED DESCRIPTION OF THE INVENTION

The methods described in U.S. Pat. No. 2,094,127, U.S. Pat. No. 2,109,844 and U.S. Pat. No. 2,241,417 supra are carried out at a reaction temperature of 200 to 400° C. at a hydrogen pressure of 100 to 300 bar to give fatty alcohols, but the desired reaction product glycerin is obtained in a small amount, and instead of glycerin, a large amount of propane, propanol or propylene glycol is obtained. DE-A 1668219 supra describes a problem that a side reaction of forming propylene glycol, propanol or propane instead of necessary glycerin cannot be regulated. In the methods described in U.S. Pat. No. 5,364,986 and U.S. Pat. No. 5,475,160 supra, 1,2-propanediol is formed in high yield, and the production of glycerin is not contemplated.

The object of the present invention is to provide an economically very excellent process for producing an alcohol by hydrogenation reaction from fats and oils as the starting material in the presence of a catalyst, wherein glycerin can be recovered in high yield.

The process for producing an alcohol according to the present invention is economically excellent and industrially very advantageous because glycerin can be recovered in high yield by suppressing decomposition of glycerin.

In the process of the present invention, the hydrogenation reaction of fats and oils is carried out in the presence of an organic solvent, and the type of the organic solvent is not particularly limited, and examples of such organic solvents include saturated hydrocarbons such as methane, ethane, propane, isobutane, butane, pentane, hexane and cyclohexane; unsaturated hydrocarbons such as ethene, propene, butene and pentene; linear alcohols such as methanol, ethanol, propanol, butanol, pentanol, hexanol, heptanol, octanol, decanol, dodecanol, tetradecanol, hexadecanol and octadecanol; branched alcohols such as isopropanol; ethers such as dimethyl ether and diethyl ether; ketones such as acetone; and carbon dioxide, and a mixed solvent of two or more of these solvents may also be used. The organic solvent or the mixed solvent may contain water. Among these organic solvents, C1 to C6 alcohols are preferable, and methanol easily separated and recovered after reaction is particularly preferable.

When the organic solvent is allowed to be coexistent, the process of the present invention is carried out under the reaction conditions where a uniform phase is not formed in the reaction system excluding a catalyst. The reaction conditions where a uniform phase is not formed can be established by temperature, pressure, the amount of the organic solvent, etc. The conditions where a uniform phase is not formed can be selected by computation with commercial phase equilibrium computing software. As the commercial software, PE2000 (Technishe Universitat Hamburg-Harburg), Prode Properties (PRODE Ltd.) and Aspen Plus (Aspentech Ltd.) are available. Also, the condition can be confirmed experimentally by measuring phase equilibrium using an autoclave.

The organic solvent used in the process of the present invention may be a supercritical fluid or a sub-critical fluid. The supercritical fluid refers to an organic solvent in the state where the partial pressure of the organic solvent is the critical pressure or more, and at the same time the reaction temperature is the critical temperature or more. The sub-critical fluid is an organic solvent in the state where the partial pressure of the organic solvent is the critical pressure or more or the reaction temperature is the critical temperature or more.

From the viewpoint of improving glycerin selectivity, the amount of the organic solvent allowed to be coexistent, in terms of the (molar) ratio of the organic solvent/fats and oils, is preferably 1 or more, more preferably 3 or more, still more preferably 6 or more. From the viewpoint of energy consumption, this molar ratio is preferably 500 or less, more preferably 300 or less, still more preferably 200 or less. When the starting fats and oils contain fatty acids etc. other than fats and oils as described later, the total of the number of moles of the fats and oils and the number of moles of compounds other than fats and oils is assumed to be the number of moles of fats and oils, and the number of moles of the organic solvent relative to this number of moles is preferably in the range described above.

The method of allowing the organic solvent to be coexistent is not particularly limited, and the organic solvent may be contained in either a gaseous or liquid state. For example, mention is made of a method of feeding the organic solvent previously mixed with the starting fats and oils into a reactor, a method of feeding the organic solvent mixed with the starting fats and oils before a reactor, and a method of adding the organic solvent during the reaction. If necessary, a combination of these methods may be used.

In the present invention, the pressure for hydrogenation reaction is preferably 1 to 50 MPa, more preferably 2 to 30 MPa. The temperature is preferably 120 to 300° C., more preferably 150 to 280° C.

The reactor used in the production process of the present invention is not particularly limited insofar as the catalytic hydrogenation reaction is feasible, and the reactor may be an ordinarily used apparatus. Examples of the reactor include a fluidized bed reactor wherein catalytic hydrogenation reaction is carried out with a catalyst dispersed in fluid, a moving bed reactor wherein catalytic hydrogenation reaction is carried out with fluid supplied while the whole of a catalyst layer drops gradually due to gravitational force, a fixed-bed reactor wherein catalytic hydrogenation reaction is carried out by supplying a fluid into a catalyst charged and fixed therein, a multi-tube fixed-bed reactor wherein the temperature of a catalyst layer can be isothermal, and a batch reactor wherein hydrogenation is carried out in a reaction vessel charged with a catalyst, starting fats and oils, and an organic solvent.

The fats and oils used as the starting material in the present invention are not particularly limited. They contain principally glycerides. The number of moles of the glycerides is referred to as the number of moles of fats and oils. The fats and oils may include not only triglyceride, but also diglyceride, monoglyceride, fatty acid etc., and it is possible to use vegetable oils such as soybean oil, rapeseed oil, coconut oil, palm oil and palm kernel oil, animal oils such as tallow and fish oil, and synthetic fats and oils. The fats and oils may be used singly or as a mixture of two or more thereof. As the fats and oils, either those subjected to pretreatment such as de-acid treatment or desulfurization treatment or those not subjected to pretreatment may be used. When fats and oils not subjected to de-acid are used, the total of the number of moles of glycerides and fatty acids is assumed to be the number of moles of fats and oils.

The catalyst used in the present invention may be a known hydrogenation catalyst or hydrogenation decomposition catalyst used in alcohol production, and is not particularly limited. For example, Co-based catalysts such as Co/Mo and Co/Zr, Cu-based catalysts such as Cu/Cr and Cu/Zn, and noble metal-based catalysts such as Re, Ru and platinum can be used. Among these catalysts, the Cu-based catalysts are preferable.

The form of the catalyst is not particularly limited and can be suitably selected from the forms of powder, granules, tablets, noodles, film, monolith, etc., depending on the type of a reactor. When a catalyst precursor is used, the catalyst is obtained by reducing it with a reducing substance. The reducing substance used here includes hydrogen, carbon monoxide, ammonia, hydrazine, formaldehyde and methanol, and these reducing substances may be used singly or as a mixture thereof and may be used in the presence of an inert gas such as nitrogen. When the catalyst precursor is to be reduced, either a gaseous phase reduction method or a liquid phase reduction method conducted in a hydrocarbon such as liquid paraffin or in an organic solvent such as dioxane, alcohol or ester may be used.

The alcohol obtained by the production process of the present invention is glycerin and a fatty alcohol derived from a fatty acid constituting the starting fats and oils, and together with the fatty alcohol, glycerin can be recovered in high yield. The simultaneously formed fatty alkyl ester can be easily hydrogenated to produce a fatty alcohol.

EXAMPLES

Figure 1:
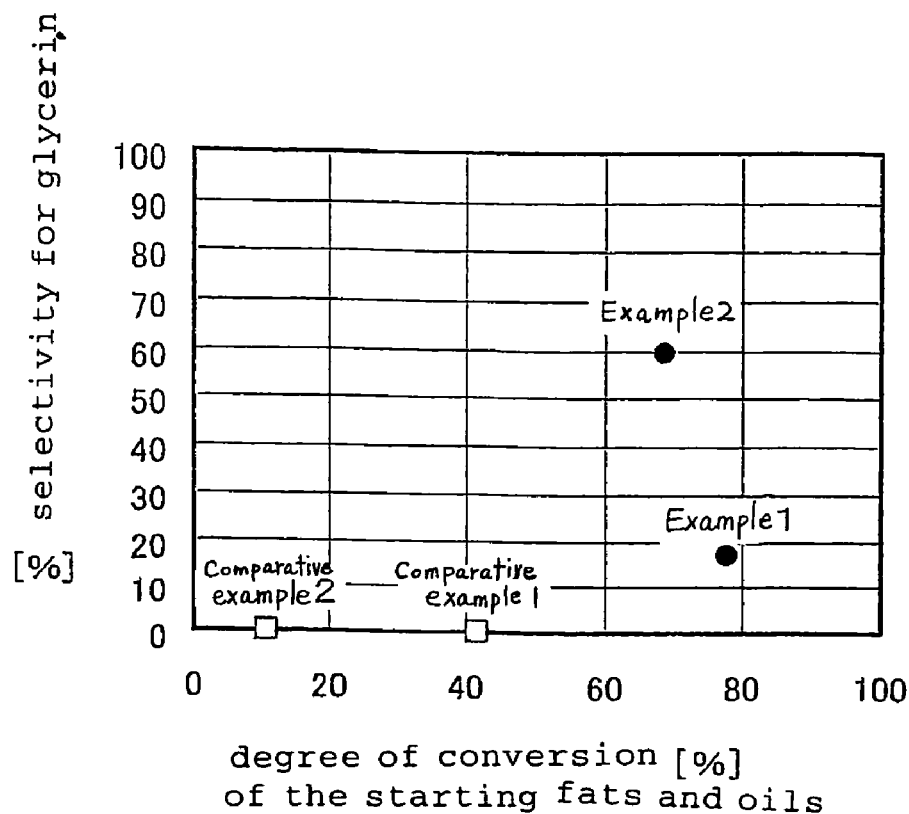
FIG. 1 shows the relationship between the degree of conversion of starting fats and oils and the selectivity for glycerin in Examples 1 to 2 and Comparative Examples 1 to 2.

The present invention is described by reference to the Examples below. The Examples are provided for merely illustrating the present invention and not intended to limit the present invention.

In the Examples and Comparative Examples below, palm kernel oil (saponification value 244.8 mg KOH/g; water content 0.05 wt %; acid value 0.17 mg KOH/g) subjected to de-acid treatment was used as the starting fats and oils.

Example 1

Using a fixed-bed reactor having an internal diameter of 13 mm charged with 30-cc Cu/Cr molded catalyst (N202D) manufactured by Nikki Chemical Co., Ltd., catalytic hydrogenation reaction was carried out under the condition of a hydrogen molar ratio of 75 to starting fats and oils at a pressure of 19.8 MPa and a catalyst layer temperature of 200° C.

Starting fats and oils were fed at a flow rate of 12 cc/hr were fed to the reactor, while methanol was fed to the reactor at such a flow rate as to be 75-molar excess to 1 mole of the starting fats and oils, and the degree of conversion of the starting fats and oils, the content of fatty alcohol in the oil phase, the content of fatty alkyl ester in the oil phase, and the selectivity for glycerin, in an outlet of the reactor, were analyzed by gas chromatography. The degree of conversion of the starting fats and oils was defined by the following equation:

Degree of conversion of starting fats and oils
(%)=100−$TGt$ wherein $TGt$ is the amount (wt %)
of triglyceride in the oil phase.

The selectivity for glycerin was defined as the ratio (wt %) of glycerin to the total organic materials in the aqueous phase detected by gas chromatography. The materials other than the fatty alcohol in the oil phase were mainly fatty alkyl ester, monoglyceride and diglyceride, and the materials other than glycerin in the aqueous phase were mainly propylene glycol, n-propanol and iso-propanol.

Example 2

According to the method in Example 1, starting fats and oils were fed at a flow rate of 12 cc/hr were fed to the reactor, while methanol was fed to the reactor at such a flow rate as to be 60-molar excess to 1 mole of the starting fats and oils, and the degree of conversion of the starting fats and oils, the content of fatty alcohol in the oil phase, the content of fatty alkyl ester in the oil phase, and the selectivity for glycerin, in an outlet of the reactor, were analyzed in the same manner as in Example 1.

Comparative Example 1

Using a fixed-bed reactor of 13 mm in inner diameter charged with 30-cc Cu/Cr molded catalyst (N202D) manufactured by Nikki Chemical Co., Ltd., catalytic hydrogenation reaction was carried out under the condition of a hydrogen molar ratio of 75 to starting fats and oils at a pressure of 19.8 MPa and a catalyst layer temperature of 200° C.

The starting fats and oils were fed at a flow rate of 12 cc/hr to the reactor, and water was added to the sample in an outlet of the reactor thereby separating the sample into an oil phase and an aqueous phase, and the degree of conversion of the starting fats and oils, the content of fatty alcohol in the oil phase, the content of fatty alkyl ester in the oil phase, and the selectivity for glycerin were analyzed in the same manner as in Example 1.

Comparative Example 2

200 g starting fats and oils were charged into a 500-ml autoclave with a rotating stirring system. Using 15 g Cu/Cr molded catalyst (N202D) (manufactured by Nikki Chemical Co., Ltd.) in a basket for the reaction, the starting fats and oils were heated to 230° C. and subjected to catalytic hydrogenation reaction for 0.2 hour under the conditions of a total pressure of 24.5 MPa and a stirring rate of 900 rpm. The catalyst used was previously activated at 1 MPa hydrogen pressure at a temperature of 200° C. for 2 hours.

Comparative Example 3

According to the method in Comparative Example 2, catalytic hydrogenation reaction was carried out for 5 hours.

Figure 2:
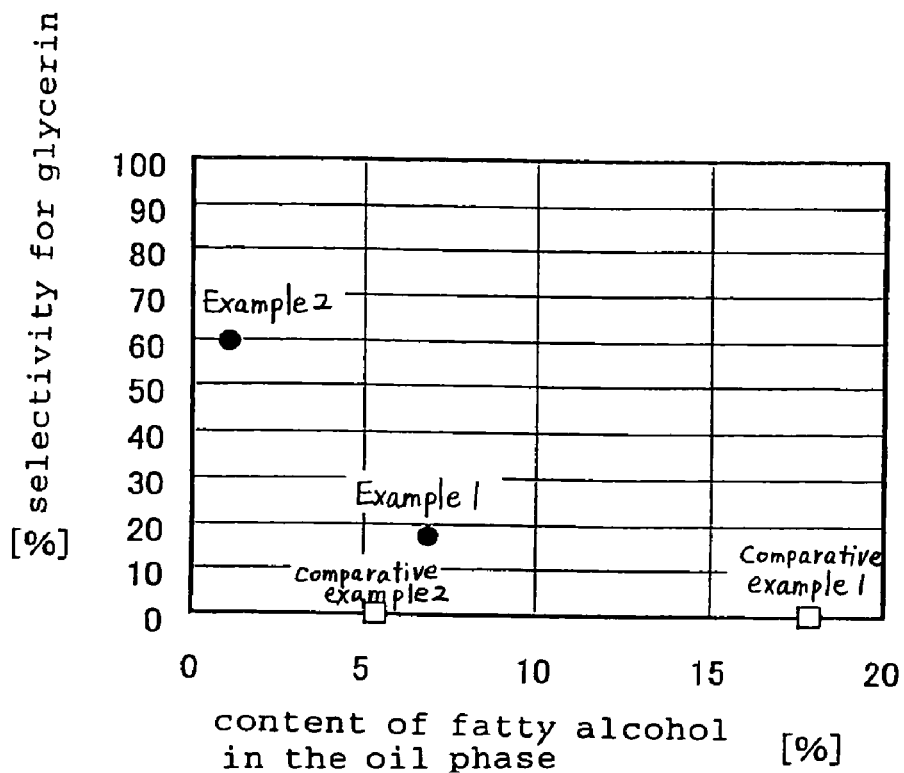
FIG. 2 shows the relationship between the content of fatty alcohol in an oil phase and the selectivity for glycerin in Examples 1 to 2 and Comparative Examples 1 to 2.

The results in Examples 1 to 2 and Comparative Examples 1 to 3 are collectively shown in Table 1. With respect to Examples 1 to 2 and Comparative Examples 1 to 2, the relationship between the degree of conversion of the starting fats and oils and the selectivity for glycerin is shown in FIG. 1, and the relationship between the content of fatty alcohol in the oil phase and the selectivity for glycerin is shown in FIG. 2.

TABLE 1

| Reactor | Example | | Comparative example | | |
|---|---|---|---|---|---|
| | 1 Fixed bed | 2 Fixed bed | 1 Fixed bed | 2 Batch | 3 Batch |
| Reaction conditions | | | | | |
| Temperature (° C.) | 200 | 200 | 200 | 230 | 230 |
| Pressure (MPa) | 19.8 | 19.8 | 19.8 | 24.5 | 24.5 |
| Hydrogen/starting fats and oils (molar ratio) | 75 | 75 | 75 | — | — |
| Methanol/starting fats and oils (molar ratio) | 75 | 60 | — | — | — |
| Reaction results | | | | | |
| Degree of conversion (%) of starting fats and oils | 78.0 | 68.8 | 41.6 | 10.8 | 99.8 |
| Content (%) of fatty alcohol in oil phase | 6.9 | 1.2 | 17.9 | 5.4 | 62.7 |
| Content (%) of fatty alkyl ester in oil phase | 62.1 | 49.7 | 3.9 | 0.2 | 26.6 |
| Selectivity of glycerin (%) | 17 | 60 | 0 | 0 | 0 |

From the results described above, it was revealed that in Examples 1 and 2, glycerin that could not be recovered in the prior art could be obtained in high yield. In Comparative Examples 1 to 3, on the other hand, the selectivity for glycerin was extremely low, independently of the degree of conversion of the fats and oils, and a majority of organic materials in the aqueous phase were decomposed products of glycerin, that is, propylene glycol, n-propanol and iso-propanol.

The invention claimed is:

1. A method for producing glycerin and a fatty alcohol comprising:
    adding an organic solvent to at least one material comprising triglyceride selected from a fat, an oil and a mixture of a fat and an oil;
    forming a nonuniform phase mixture of the organic solvent and the at least one material comprising triglyceride;
    hydrogenating the nonuniform phase mixture in the presence of a catalyst; and
    recovering glycerin;
    wherein
    a mole ratio of the organic solvent to the at least one material comprising triglyceride is from 1 to 500,
    the organic solvent increases a selectivity for glycerin, and is at least one solvent selected from the group consisting of a saturated hydrocarbon, an unsaturated hydrocarbon, a linear alcohol, a branched alcohol, an ether, a ketone and carbon dioxide.

2. The method of claim 1, wherein the organic solvent is a linear alcohol or a branched chain alcohol comprising 1-6 carbons.

3. The method of claim 2, wherein the alcohol is methanol.

4. The method of claim 1, wherein the organic solvent comprises water.

5. The method of claim 1, wherein the catalyst is at least one selected from the group consisting of a Co based catalyst, a Cu based catalyst, a Re based catalyst, a Ru based catalyst and a Pt based catalyst.

6. The method of claim 5 wherein the catalyst is a Cu based catalyst.

7. The method of claim 6, wherein the Cu based catalyst is one selected from the group consisting of Cu/Cr and Cu/Zn.

8. The method of claim 1, wherein the hydrogenating is at a pressure of from 1 MPa to 50 MPa.

9. The method of claim 8, wherein the pressure is 2 MPa to 30 MPa.

10. The method of claim 1, wherein the hydrogenating is at a temperature of from 120° C. to 300° C.

11. The method of claim 10, wherein the temperature is from 150° C. to 280° C.

12. The method of claim 1, wherein the mole ratio of the organic solvent to the at least one material comprising triglyceride is from 3 to 300.

13. The method of claim 1, wherein the mole ratio of the organic solvent to the at least one material comprising triglyceride is from 6 to 200.

14. The method of claim 1, wherein the selectivity of glycerin is at least 17%.

* * * * *

UNITED STATES PATENT AND TRADEMARK OFFICE
CERTIFICATE OF CORRECTION

PATENT NO.       : 7,667,059 B2                                          Page 1 of 1
APPLICATION NO.  : 11/367340
DATED            : February 23, 2010
INVENTOR(S)      : Sakamoto et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 560 days.

Signed and Sealed this

Seventh Day of December, 2010

David J. Kappos
*Director of the United States Patent and Trademark Office*